(12) United States Patent
Ward

(10) Patent No.: US 7,260,586 B1
(45) Date of Patent: Aug. 21, 2007

(54) METHOD AND SYSTEM FOR HOME MEDICAL MANAGEMENT

(76) Inventor: Stephanie Ward, 76 E. Mountain Rd., Neshanic Station, NJ (US) 08853

( * ) Notice: Subject to any disclaimer, the term of this patent is extended or adjusted under 35 U.S.C. 154(b) by 0 days.

(21) Appl. No.: 09/458,899

(22) Filed: Dec. 10, 1999

(51) Int. Cl.
*G06F 17/00* (2006.01)
*G06F 19/00* (2006.01)

(52) U.S. Cl. ........................ 707/104.1; 705/2
(58) Field of Classification Search ............ 707/104.1, 707/10, 100; 705/2, 3, 4; 40/124, 124.4; 206/528, 538, 533, 540; 221/203, 9
See application file for complete search history.

(56) References Cited

U.S. PATENT DOCUMENTS

| | | | |
|---|---|---|---|
| 3,792,542 A | | 2/1974 | Cohan |
| 3,921,318 A | | 11/1975 | Calavetta |
| 4,236,332 A | | 12/1980 | Domo |
| D284,581 S | | 7/1986 | Peterson |
| 4,621,729 A | | 11/1986 | Jackson |
| 4,632,428 A | | 12/1986 | Brown |
| 5,031,937 A | * | 7/1991 | Nellhaus ............... 283/52.1 |
| 5,171,039 A | | 12/1992 | Dusek |
| 5,197,763 A | | 3/1993 | Whalen |
| 5,597,182 A | | 1/1997 | Reber et al. |
| 5,659,741 A | | 8/1997 | Eberhardt |
| 5,758,096 A | | 5/1998 | Barsky et al. |
| 5,995,938 A | * | 11/1999 | Whaley ................... 705/3 |
| 6,112,986 A | * | 9/2000 | Berger et al. ............. 705/4 |
| 6,421,650 B1 | * | 7/2002 | Goetz et al. ............. 705/3 |
| 2005/0218152 A1 | * | 10/2005 | Simon ................... 221/203 |

FOREIGN PATENT DOCUMENTS

| | | | |
|---|---|---|---|
| DE | B 42 D 15/04 | | 8/1993 |
| FR | 2 375 680 | | 7/1978 |
| FR | 2 494 871 | | 5/1982 |

* cited by examiner

*Primary Examiner*—Sam Rimell

(57) ABSTRACT

The present invention relates to a method and system for home medical management in which a report, a one-page, one-sided, printed record visible by the naked eye of medical and personal emergency information is generated. The report is adapted to be used on a daily basis and carried on the person. A first template is provided for entering first data related to emergency contact information, medical history information and personal information. A second template is provided for entering second data related to medication information. The first and second data are mapped to predetermined locations of the report. The report is generated to include the emergency contact information in an emergency contact section, the medical history information in a medical history section, the personal information in a personal information section and the medication information in a medication information section. The first template can also provide for entering of data related to insurance information and pharmacy information and other types of information. The medication section of the report can include rows representing each type of medication by name. The medication section can also include columns directed to a graphic illustration of each medication, the dosage, the physician prescribing the information and the time of the day for taking each medication. The report can be used as a life saving device in an emergency situation to provide emergency personnel with required information. The report can be also used during doctor visits and hospital stays to eliminate mistakes and on a daily basis to manage the individual's taking of medications.

1 Claim, 11 Drawing Sheets

Stephanie Ward    Serial #: 09/458,899

This LifeReport For:        18        READ IN EMERGENCY                        Lifereport Date: 11/10/00    24

John Smith 20                22      Born: 8/30/00    Age: 75    SSN: 100-10-1000    Blood Type: A+
60 Sunnymead Rd.                         Height: 5'8"    Weight: 162    Normal Blood Pressure: 140/80
Somerville, NJ 08876    908-555-6358     ☒ Tetanus Shot:         □ Pneumonia Shot:    ☒ Flu Shot: 10/99
Work:                     Fax: 908-555-0137
Insured By: Medicare A&B    Group #:
31   ID#: 100-10-1000
Secondary: United Health    Group #:    ☒ Living Will □ Organ Donor □ DNR Location: Bangbox, Stephanie has.

*Allergies* 35a
QUINICLITE: swelling of feet & hands, dizziness & joint pain. 12/98
PROCANAMIDE SR & PROCANBID 1000 mg BID swelling of feet & hands, dizziness & joint pain. 10/00/98
SINEMET: drowsy faint. LOW BP, sweaty, nausea 7/25/99. Decreased to 1/2 pill. New Pack to 1 3x5.

25 *Schedule of Medications* (including Non-Prescription & Supplements)

| | | | | | Morning Before Breakfast | Morning After Breakfast | Afternoon 2:00 | Evening 6:00 | Bedtime 10:00 |
|---|---|---|---|---|---|---|---|---|---|
| 26a | Pepcid | 27 (20 mg) | 28 Dr Mahaf | | ○ | | | | |
| 26b | Capoten | (25 mg) | Dr. Mahaf | empty stomach | ○ | | ○ | ○ | ○ |
| 26c | Sinemet CR | (50/200) | Dr Friedlander | from 10 to 1 pill 8/19/99 | ○ | | ○ | ○ | ○ |
| 26d | Amantadine | (100 mg) | Dr Friedlander | 1/2 pill to 1/2 9/99 | ○ | | ○ | ○ | ○ |
| 26e | Mysoline | (Vitamin) | Dr Meleos | | | ○ | | | |
| 26f | Baby Aspirin | (81 mg) | Dr. Mahaf | | ○ | | | | |
| 26g | Lanoxin | (0.25 mg) | Dr Mahaf | | ○ | | | | |
| 26h | ABC Plus Senior | (Vitamin) | Dr Meleos | | ○ | | | | |
| 26i | Lasix (Furosemide) | (20 mg) | Dr. Mahaf | 2nd tab with juice | | | | ○ | ○ |
| 26j | Coumadin | (5 mg) | Dr. Mahaf | | | | | ○ | ○ |
| 26k | Transderm Nitro | (0.2 mg/hr) | Dr Mahaf | Apply 8 AM Remove 8 PM | | | | | |

*Current Medical Conditions* 35b
DIABETES: 10/99
HEART DISEASE: Wears DEFIBRILLATOR. 2/XX/98
HERNIA: where Cordiaquis did not heal. 11/97
ANEURYSM: in heart wall. Dr. Mahaf 8/12/96
PARKINSON'S: diagnosed by Dr. Greenberg, Somerville. Took Sinemet & Artane 9/11/93

*Surgeries & Procedures* 35c
DEFIBRILLATOR IMPLANT: AICD Dr. Poininger, RWJ Hart of digestive heart failure. 2/2/98
ESOPHAGUS CANCER: Dr. Diehl, Morristown. Partial removal. Chemo 9/11/96
ANGIOPLASTY & STENT: Dr. Mahaf, Morristown. Aneurysm in heart wall 8/12/96
ANGIOPLASTY: Dr. Cruny, Newark Beth Israel. 10/18/89

36 *Medications PRN "When Needed"*
| Nitrostat | 0.3 mg tab | Dr. Mahaf |
| Tylenol | | |

32 *Physicians*
| | Phone | Specialization | Fax | City/State |
|---|---|---|---|---|
| Dr. Hewton Nahan | 908-555-0632 | Family Doctor | 908-231-0688 Somerville, NJ | |
| Dr Shaun S. Mahaf | 908-555-8668 | Cardiologist | 908-271-8766 Bridgewater, NJ | |
| Dr Mark Precongur | 732-555-7208 | Gastroenterologist RWJ | | New Brunswick, NJ |
| Dr Mark Pressheer | 732-555-7706 | Oncologist | | |
| Dr. Freddander | 732-555-1300 | Neurologist | | East Brunswick, NJ |
| Dr. Without Diehl | 973-555-6400 | Oncologist | 973-261-7295 Morristown, NJ | |
| Dr Deeng | 973-555-1850 | Ear, Nose, Head | | Montclair, NJ |

30 *In Case of Emergency... Call:*
Stephanie Ward ... Daughter ... 908-555-3837
Work: 908-359-1114 Cell Phone:
Peter M. Hindrick ... Son ... 908-555-6358
Work: Cell Phone:
Marge Jarkowski ... Companion 908-555-8592
Work: 908-555-9213 Fax: 33
Rchert Pharmacy
Notice: Please check that your Lifereport contains all your needed information and that it is current. Review with your physician or family care provider if there is a problem with the medicine, phone contact or address at 877-454-1531 or visit our website    www.lifereport.com

*Past Medical Conditions* 35d
DEHYDRATION: lowered Lasix. 8/27/00
DEPRESSION: 10 mg. Paxil from approx. 2/98 to 8/98
HEART ATTACK. 11/28/89

Fig. 2

The Question & Answer Session I: *(Preliminary Information)* begins with:

1. What is the name of the person for whom this LifeReport is being created?
2. The birth date?
3. The permanent address?
4. The phone number?
5. The fax number?
6. The E-Mail address?
7. Is there another residence? ____ yes _____ no If yes, questions 3 thru 7 repeated until a no answer is given.
8. The Social Security #?
9. The Blood Type?
10. The Primary Insurance Carrier?

Name: _____ Identification #:_____

Group #:_____ Phone #:_____
11. The Secondary Insurance Carrier, if any?

Name: _____ Identification #:_____

Group #:_____ Phone #:_____
12. In Case of Emergency, who should be contacted? (please limit your choices to no more than six)

Phone: _____ Relation: _____ ___day ___evening
        Phone: _____ Relation: _____ ___day ___evening
        Phone: _____ Relation: _____ ___day ___evening
        Phone: _____ Relation: _____ ___day ___evening
        Phone: _____ Relation: _____ ___day ___evening
        Phone: _____ Relation: _____ ___day ___evening 13. Your Pharmacy?
    Name: _____ Phone #: _____

14. Alternate Pharmacy?
    Name: _____ Phone #: _____

15. The Physicians?
    Name: _____ Type of Physician: _____
    Address: _____
    Phone #. _____ Fax #: _____

16. Is there another Physician? _____ yes _____ no
    If yes, question 15 is repeated until a no answer is given.

17. Is there any Allergies?
    Allergic to: _____

18. Is there another Allergy? _____ yes _____ no
    If yes, question 17 is repeated until a no answer is given.

19. Is there any Medical Conditions?
    Medical Condition: _____
    Diagnosed by: _____ On: _____

20. Is there another Medical Condition? _____ yes _____ no
    If yes, question 19 is repeated until a no answer is given.

21. Is there any Diseases?

Cont. Fig. 4a

Disease: _____

Diagnosed by: _____ On: _____

22. Is there another Disease? ____ yes _____ no

If yes, question 21 is repeated until a no answer is given.

23. Was there any Surgical Procedures?

Surgical Procedure: _____

Attending Physician: _____

Date of Surgery: _____

At What Hospital: _____

Outcome: _____

24. Is there another Surgical Procedure? ____ yes _____ no

If yes, question 23 is repeated until a no answer is given.

25. Is there Medical Alerts such as Pacemakers, Defibrillators, Insulin Dependency?

Please Describe: _____

26. Is there another Medical Alert? ____ yes _____ no

If yes, question 25 is repeated until a no answer is given.

The Question & Answer Session 1: *(Preliminary Information)* is complete.

Fig. 4b

The Question & Answer Session II: *(Prescription Regimen)* begins.

Please supply the information directly from the prescription or non-prescription bottle label. Prescription drugs include non-prescription drugs, if they are prescribed by a physician.

1. What is the prescription drug?

Name:_____

Dosage:_____

Prescribing Physician:_____

Physician's Orders: _____

Date The Prescription was Filled:_____

2. Is there another Prescription Drug? ____ yes ____ no

If yes, question 1 is repeated until a no answer is given.

3. What is the non-prescription drug?

Name:_____

Dosage taken: _____

Recommended Dosage:_____

Physician's Orders: _____

4. Is there another Non-Prescription Drug? ____ yes ____ no

If yes, question 1 is repeated until a no answer is given.

5. What is the earliest time of the day a drug will be taken or given?

6. What is the latest time of the day a drug will be taken or given?

The Question & Answer Session II: *(Prescription Regimen)* is complete.

*John Smith*    SS#: 100-10-1000

How To Arrange Your Pillbox .... Your PILL BOX MAP

PATCH Transderm Nitro    (0.2 mg/hr)    *Dr. Mulud*    Apply 9 AM — Remove 9 PM

| EVENING<br>8:00 p.m.<br><br>PEPCID   CAPOTEN   COUMADIN<br>SINEMET   AMANTADINE<br>LASIX | MORNING<br>*Before Breakfast*<br><br>PEPCID   CAPOTEN<br>SINEMET   AMANTADINE |
|---|---|
| AFTERNOON<br>2:00 p.m.<br><br>CAPOTEN<br>SINEMET   AMANTADINE | MORNING<br>*After Breakfast*<br><br>BABY ASPIRIN   LANOXIN<br>ABC Plus SENIOR VITAMIN   MAGOXIDE |

Fig. 6

The HOME MEDICAL MANAGER
© 1999

John Smith SS#: 109-10-1000
Will You Have Enough Pills for Your Trip?.... Your TRIP PLANNER Today's Date: November 15, 1999  
Trip Start Date: December 1, 1999  
Trip End Date: December 8, 1999  
Duration of Trip: 7 Days No matter what time you leave for your trip...
Take your trip medications starting in the morning of December 1, 1999.

It's a good idea to take along 1 extra in case you lose a dose or are delayed.

| Medications (including Non-Prescriptions & Supplements) | | Date Filled | Doses per Prescription | Doses per Day | Days Left after today | Prescription Empties On | Earliest Refill Day for Trip | Doses to take for Trip |
|---|---|---|---|---|---|---|---|---|
| Pepcid | (20 mg) Dr. Michel | 11/01/99 | 60 | 2 | 15 | 11/30/99 | 11/23/99 | 17 |
| Capoten | (25 mg) Dr. Michel | 11/01/99 | 90 | 3 | 45 | 12/15/99 | 12/08/99 | 25 |
| Sinemet CR | (50/200) Dr. Friedlander | 11/01/99 | 90 | 3 | 45 | 12/15/99 | 12/08/99 | 25 |
| Amantadine | (100 mg) Dr. Friedlander | 11/01/99 | 90 | 3 | 45 | 12/15/99 | 12/08/99 | 25 |
| Minoxide | (Vitamin) Dr. Newton | 11/01/99 | 100 | 1 | 85 | 02/12/00 | | 7 |
| Baby Aspirin | (81 mg) Dr. Michel | 10/25/99 | 100 | 1 | 79 | 01/18/00 | | 7 |
| Lanoxin | (0.25 mg) Dr. Michel | 11/01/99 | 30 | 1 | 15 | 11/30/99 | 11/23/99 | 7 |
| ABC Plus Senior | (Vitamin) Dr. Newton | 10/01/99 | 100 | 1 | 64 | 01/08/00 | | 7 |
| Lasix (Furosemide) | (20 mg) Dr. Michel | 11/01/99 | 30 | 1 | 15 | 11/30/99 | 11/23/99 | 7 |
| Coumadin | (5 mg) Dr. Michel | 10/20/99 | 20 | 1 | 4 | 11/19/99 | 11/12/99 | 7 |
| Transderm Nitro | (0.2 mg/hr) Dr. Michel | 10/25/99 | 60 | 1 | 39 | 11/20/99 | 11/13/99 | 7 |

All Medications marked with X need refills before your trip.

Eckerd Pharmacy  908-231-9223  Fax:

Advice: Refill all needed medications at the same time.... 11/20/99.

Fig. 8

The HOAF MEDICAL MANAGER © 1999

METHOD AND SYSTEM FOR HOME MEDICAL MANAGEMENT

BACKGROUND OF THE INVENTION

1. Technical Field

The present invention relates to a computer-based system and method for managing a person's medical and personal emergency information.

2. Related Art

In the area of health care in which the number of patients typically outnumber the number of doctors, there is a growing need for personal management of a person's medical history and present medical status in order to avoid confusion and mistakes by health care personnel. For example, in an emergency situation in which a patient is under stress or impaired, it is desirable that the patient have a printed record carried on their person carrying critical information which can be read by emergency personnel. Also, it is desirable for the client to include medication information which can be read by the emergency personnel.

Several patents disclose personal anatomy cards including a machine readable storage medium. U.S. Pat. No. 5,597,182 describes a personal anatomy card in which a card is sized for carrying on the individual. A machine readable storage medium stores human anatomy information used for medical treatment or personal identification. A data player which is external to the card or integrated in the card views the stored data.

U.S. Pat. Nos. 4,236,332 and 3,921,318 describe a medical record card having indicia visible to the human eye for critical emergency information and having indicia visible by use of a microfilm reader for detailed personal identification data and medical history data. The above described patents have the draw back that a display or data reader device is needed for accessing medical history data making substantial portions of the information unavailable to emergency personnel not having access to the data reader and the medical history information is also unavailable for home use by the individual.

U.S. Pat. No. 5,758,096 ('096) describes a computer based system and method for generating a medication management display. A plurality of medication names prescribed for a patient with corresponding strengths attributes and alpha numeric medication symbol attributes are entered into an electronic database. An electronically stored correlation list is then accessed to associate the alphanumeric symbol attributes to graphic symbols. The information is arranged to generate a patient medication chart displaying one or more medication names associated with its corresponding strength, directions and graphic symbol. Adhesive graphic symbols are applied to the original medication containers that hold the medications to cross-reference the actual medications with the chart. The patient medication data may also include administrator's comments. The '096 patent has the limitation of being cumbersome to understand and not including emergency information or detailed personal information which information is critical in emergency situations.

It is desirable to provide a home medical management system capable of producing a report integrating medical history information, personal information and medication information on a one-page, one-sided, printed record visible by the naked eye which can be used on a daily basis to assure safe and correct administering of prescription and non-prescription drugs and can be used in an emergency situation, which report can be easily updated and displayed as a hard copy.

SUMMARY OF THE INVENTION

The present invention relates to a method and system for home medical management in which a report, a one-page, one-sided, printed record visible by the naked eye of medical and personal emergency information is generated. The report is adapted to be used on a daily basis and carried on the person. A first template is provided for entering first data related to emergency contact information, medical history information and personal information. A second template is provided for entering second data related to medication information. The first and second data are mapped to predetermined locations of the report. The report is generated to include the emergency contact information in an emergency contact section, the medical history information in a medical history section, the personal information in a personal information section and the medication information in a medication information section. The first template can also provide for entering of data related to insurance information and pharmacy information and other types of information.

The medication section of the report can include rows representing each type of medication by name. The medication section can also include columns directed to a graphic illustration of each medication, the dosage, the physician prescribing the information and the time of the day for taking each medication. A database can be accessed to provide information on attributes of the medication which information can be used in generating the report. The database can include medication interaction information and a second report of an alert of drug interactions can be generated if medication interaction is found. The database can also include general information about the drug which can be generated on the report.

The method and system can also provide for a pillbox map for determining the most efficient method of placement of pills in a pillbox. In addition, the method and system can provide a travel planner report for scheduling the amount of medication that will be needed during travel and the optimum times for refilling of the medication to assure that there will be no lapse of medications available.

The system has the advantages of managing, categorizing and displaying an individuals entire medical and personal status in an easy to create and easy to read format. The report can be used as a life saving device in an emergency situation to provide emergency personnel with required information. The report can be also used during doctor visits and hospital stays to eliminate mistakes and on a daily basis to manage the individual's taking of medications. Since the report is created by the patient and/or guardian/caregiver, there is no limit to the amount of reports available, or the amounts of updates/revisions available. The reports can be carried on the patient and freely distributed to all necessary personnel and family members. The invention will be more fully described by reference to the following drawing.

BRIEF DESCRIPTION OF THE DRAWINGS

FIG. 2 is a schematic diagram of a report generated by the HMM system.

FIG. 4A is a template for inputting personal and emergency information.

FIG. 4B is a template for inputting medication information.

FIG. 6 is a schematic diagram of a pillbox report generated by the HMM system.

FIG. 8 is a schematic diagram of a travel medication planner report generated by the HMM system.

DETAILED DESCRIPTION

Figure 1:
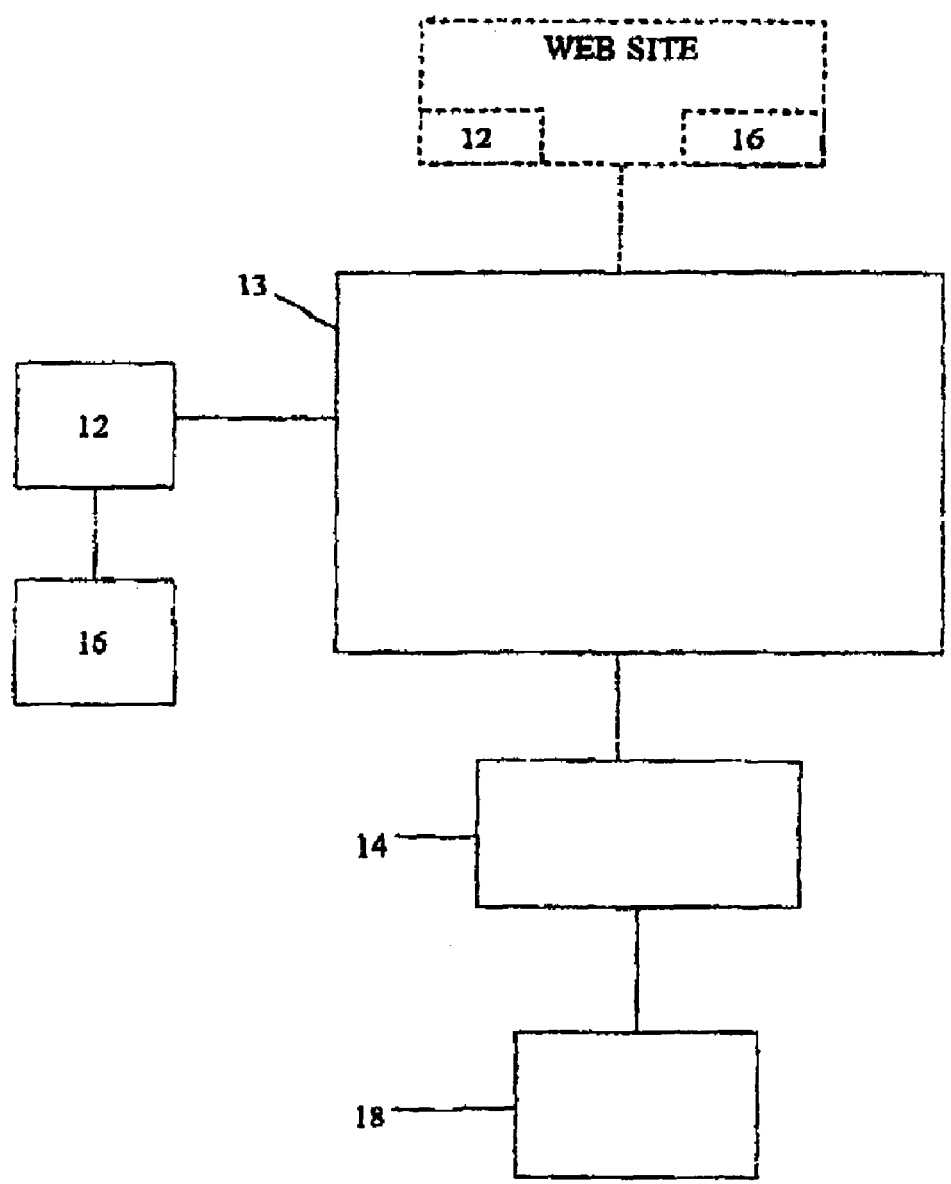
FIG. 1 is a schematic diagram of a home medical management HMM system in accordance with the teachings of the present invention.

FIG. 1 illustrates home medical management (HMM) system 10 in accordance with the teachings of the present invention. Home medical management (HMM) software 12 is executed on general personal computer 13, such as a central processor unit and memory or on a CD-ROM. Alternatively, HMM software 12 is stored at a web site of the world web (WWW). HMM software 12 can be accessed at the web site over the Internet. The advantage of internet usage is that HMM software 12 can be accessed anywhere, at any time by a physician or health care provider at the patient's request. It can then be updated right in the physician's office if necessary. In Internet usage access to a user's profile is controlled by a password created by the patient which password can be modified by the patient at any time.

Output device 14 is electronically connected to HMM software 12. For example, output device 14 can be a color laser printer. HMM software 12 interfaces database 16 for storing and retrieving data.

Report 18 can be generated by HMM software 12, as defined below. Report 18 can be printed by output device 14 as a hard copy. Preferably, the hard copy of report 18 is a single sheet of letter size paper, which can be read by the individual, by the human eye, folded to a credit card size and carried on the person for example in a wallet or purse. When folded the indicia "Read In Emergency" appear in a readily visible location on report 18 to alert medical personnel to read report 18. Alternatively, report 18 can be stored on an electronic medium and printed on an alternative output device.

FIG. 2 illustrates an example of report 18. Name section 20 sets forth the name of the individual for which report 18 is generated. Critical personal information section 22 sets forth information, which is needed by emergency personnel or health care workers in an emergency situation or for treatment. Suitable information included in critical personal information section 22 is birth date, social security number, blood type, address, home telephone number and work telephone number. Personal information section 24 includes personal information of the individual such as blood pressure, height, weight, eye color, hair color, and the like. Personal Information section 24 can also include legal preferences such as if the individual has a living will document, if the individual has an organ donor document or if the person has a do not resuscitate document and the location of these documents.

Medication section 25 lists medications taken by the individual. Names of medications are set forth in rows 26a-26k of medication section 25. A graphical symbol illustrating the shape and size of the medication can be included in each respective row 26a-26k. The geographical symbol can illustrate the shape of the medication such as round, oval, octagonal, polygonal, rectangular and the like, the size of the medication such as long, small, tiny, very large and the like, and the color such as red, white, orange and the like. Medication section 25 can include strength (dosage) column 27 indicating the strength of the medications respectfully listed in rows 26a-26k. Prescribing physician column 28 can be included in medication section 25 indicating the physician that prescribed the medications respectfully listed in rows 26a-26k and physicians comments. Time section 29 indicates the time of the day for taking each respective medication listed in rows 26a-26k. For example, time section 29 can include headings for "Morning before breakfast", "Morning after breakfast", "Afternoon", "Evening" and "Bedtime." It will be appreciated that exact times, i.e. Afternoon 1:00, can be customized by each patient by interacting with HMM software 12.

Emergency contact section 30 sets forth individuals to be contacted in case of emergency. For example, emergency contact section 30 can include an emergency contact's name, relationship to the individual listed on report, home phone number, work phone number and cellular phone number.

Insurance information section 31 includes insurance information of the individual. For example, the insurance information can include the name of the insurance carrier, the group policy number and individual identification number.

Pharmacy information section 33 indicates pharmacy information of the individual. For example, the pharmacy information can include the name of the individual's pharmacy, phone number of the pharmacy and name of the pharmacist.

Medical history in sections 35a-35d sets forth present and historical medical conditions of the individual as listed in rows 35a-35d. Rows 35a-35d can include information directed to allergies, reactions from the allergies, treatment for the allergies, diagnosed medical conditions and historical medical procedures performed on the individual.

When needed, non-prescription and supplements section 36 sets forth information related to non-prescription medication and supplements used by the individual. For example, non-prescription and supplements section 36 can describe medications that may be prescribed, such as codeine, but are only to be used for pain as needed, not on a regimented basis.

Figure 3:
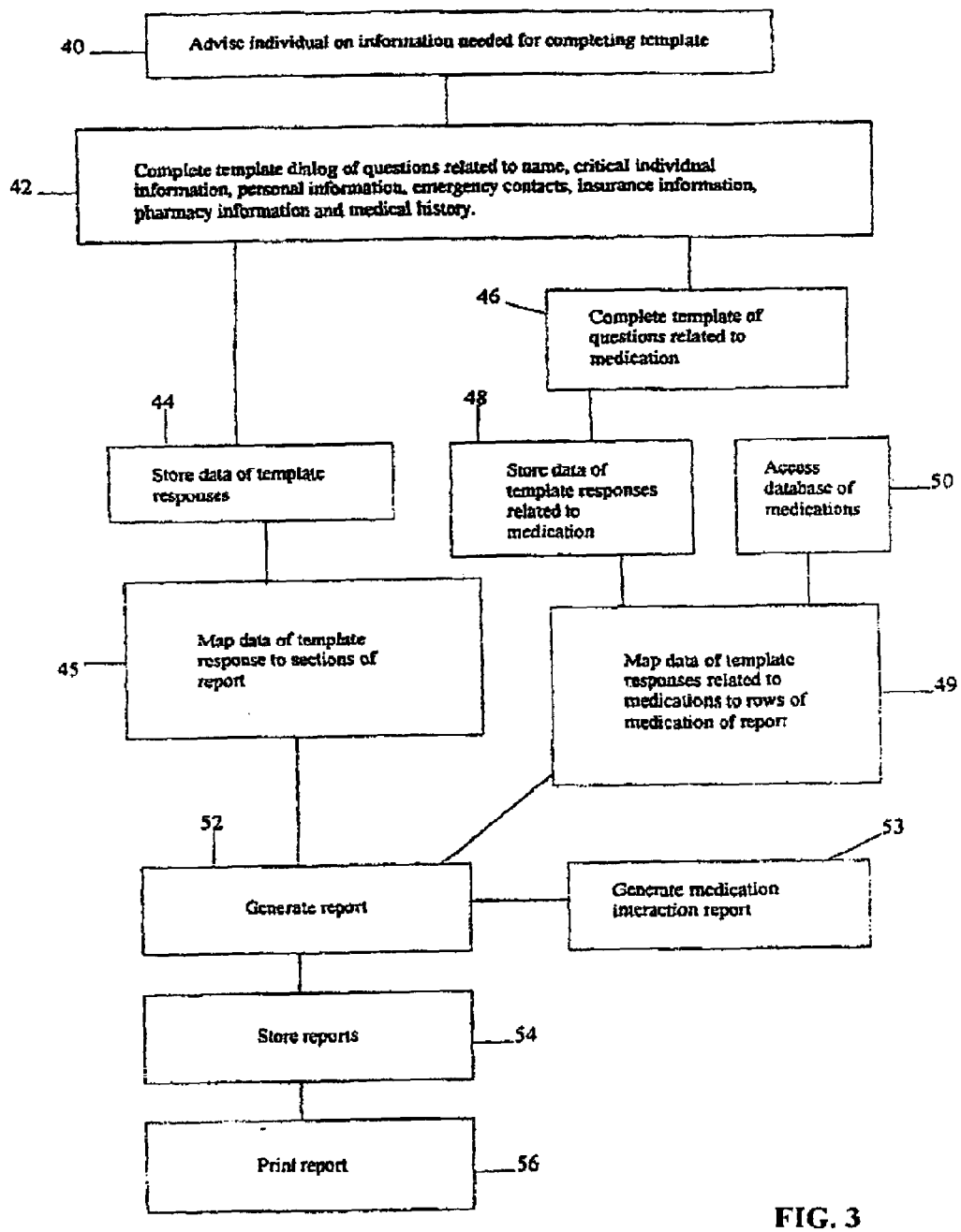
FIG. 3 is a flow diagram of operation of the HMM system and method for generating a report.

FIG. 3 is a flow diagram of operation of the system and method in accordance with the present invention. In block 40, the individual is advised of information needed for completing report 18 to be generated by HMM System 10. Block 40 can be executed by HMM software 12 to generate messages or screen displays indicating the types of information helpful for completing templates, as described below. For example, the individual can be advised to locate the resources of a social security card, insurance card, phone book, and labels from prescription bottles.

In block 42, a template is completed directed to questions related to name, critical personal information, personal information, medication, emergency contacts, insurance information, pharmacy information and medical history. An example of a template useful for block 42 is shown in FIG. 4a. Data input into the template completed in block 42 is stored in HMM software 12 in block 44. For example, data input into the template can be stored in a table or database.

It will be appreciated that the size or number of rows of information in each section of report 18 can be varied in order to adequately display an individual's information.

In block 45, data stored for the template completed in block 42 is mapped to predetermined locations of a report. For example, data can be mapped to respective sections of name section 20, critical personal information section 22, personal information section 24, emergency contact information section 30, insurance information section 31, pharmacy information section 32, medical history section 34 and when needed, non-prescription and supplements section 36.

In block 46, a template is completed directed to questions related to medication used by the individual. An example of a template useful for block 46 is shown in FIG. 4B. Data input into the template completed in block 46 is stored in HMM software 12 in block 48. In block 49, data stored for the template completed in block 46 is mapped to rows 26a-26j and columns 27-29 at medication section 25 of report 18. Block 49 can also access a database of medications 50 for providing additional information on the medication. For example, database of medications 50 can include entries of commonly prescribed drugs and non-prescription drugs and information related to the medication such as the shape, size and color, interaction with other medications, preferable times for taking the medication, and possible side effects. The information from database 50 is also mapped to rows 26a-26j and columns 27-29 of medication section 25.

Block 52 is executed to generate a report 18 by combining the mapped data of block 45 with the mapped data of block 49. In block 53, a medication interaction report can be generated advising the individual, if any of medications listed in report 18 have interactions to one another. For example, medication interaction report 53 can list the names of the medications that have interactions to one another. The medication interaction report 53 can include an indication to the individual to consult with their physician on the determined medication interaction. The report generated in block 52 and the report generated in block 53 can also be stored on the user's personal computer in block 54. For example, a data file electronically storing report 18 can be stored under the individual's social security number. In block 56, HMM software 12 generates an electronic or hard copy output in the form of report 18 shown in FIG. 2 and a medication interaction report 53 if any medication listed in report 18 have interactions to one another.

Figure 5:
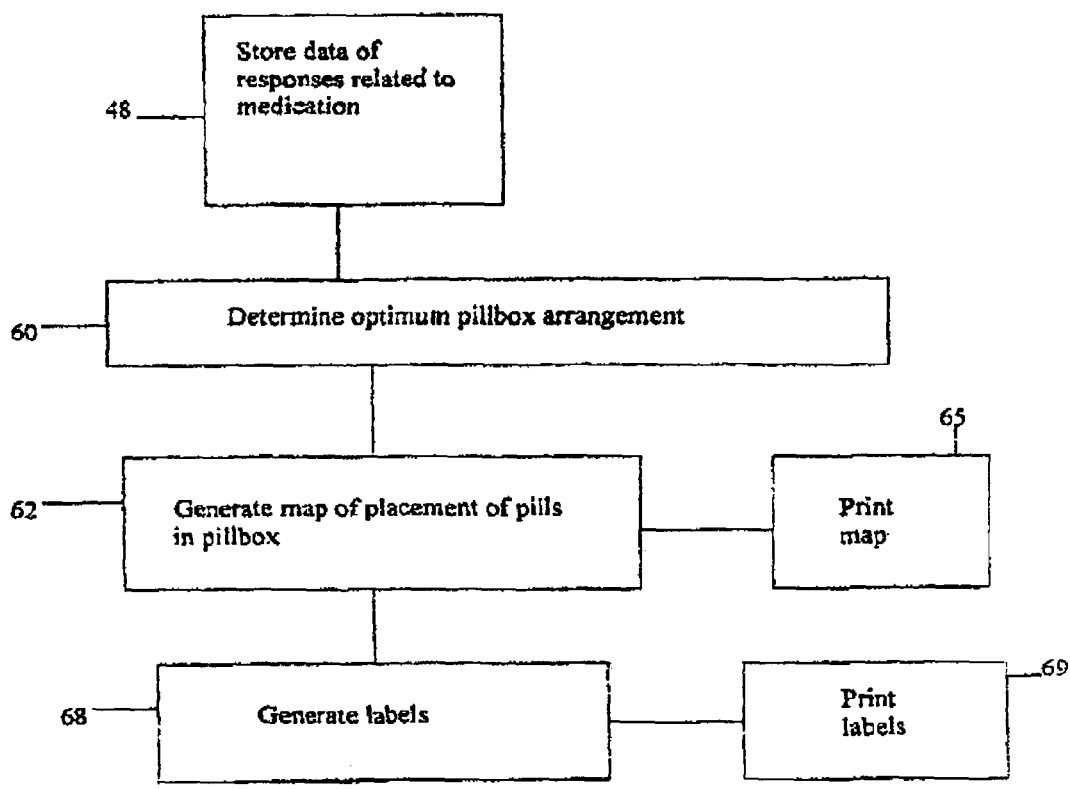
FIG. 5 is a flow diagram of operation of the HMM system for generating a report for placement of medication in a pillbox.

FIG. 5 illustrates a flow diagram of operation of HMM system 10 for generating a map for placement of medications in a pillbox. Block 60 uses input of block 48 of data related to medications which is input into the template in order to determine an optimum pill box arrangement. For example, block 60 can determine the optimum pillbox arrangement for any pillbox manufactured i.e., if one box per week with seven divisions or seven boxes per week with four divisions are used.

In block 62 a pillbox map 64 is generated by HMM software 12. The pillbox map 64 can be printed in block 65. FIG. 6 is schematic diagram of pillbox map 64. Pillbox map includes respective sections 66a-66d corresponding to time section 29 of report 18. Graphical symbols included in each row 26a-26j are mapped to respective section 66a-66d. In block 68, HMM system 10 can generate adhesive labels indicating the name of each medication, the time for taking each medication. The labels can be printed, for example, on adhesive backed materials in block 69 and can be applied to the original container of the medication.

Figure 7:
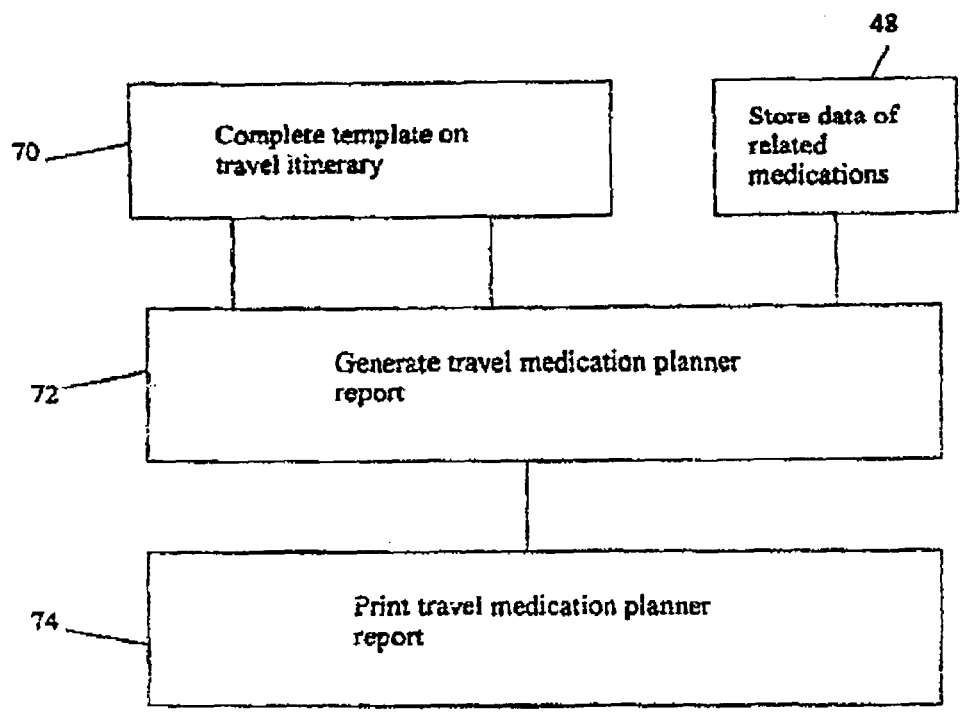
FIG. 7 is a flow diagram of operation of the HMM system for generation of the HMM system for generating a travel medication planner report.

FIG. 7 illustrates a flow diagram of operation of HMM system 10 for providing a travel medication planner report. In block 70, the individual completes a template directed to questions related to the travel itinerary. For example, the template can include questions on the trip start date, trip end date, dates prescription was filled and amount of dosages in prescription. Block 72 uses input of block 48 of data related to medications which is input into the template in order to generate a travel medication planner report 73 which associates the medications with the length of stay of the travel itinerary In block 74, travel medication planner report 73 is printed by output device 14.

FIG. 8 illustrates an example of travel medication travel report 73. Section 75 sets forth the required number of dosages needed for the length of time of the trip. Section 76 sets forth a marking if the medication set forth in rows 26a-26k must be refilled before the start date of the trip. Section 77 sets forth the refill date before the date of the trip. Accordingly, if an entry appears in section 75 and section 77 the medication must be refilled before the date of the trip. Prescription data section 78a and section 78b sets forth respectively the date the prescription was filled and doses per prescription for each of the medications listed in rows 26a-26k. Section 78c sets forth the dosages taken per day. Section 78d sets forth the days left in the prescription after the date the report is generated. 78e sets forth the date the prescription is emptied.

It is to be understood that the above-described embodiments are illustrative of only a few of the many possible specific embodiments, which can represent applications of the principles of the invention. Numerous and varied other arrangements can be readily devised in accordance with these principles by those skilled in the art without departing from the spirit and scope of the invention.

I claim:

1. A computer readable medium storing a program which controls a computer system, the program causing the computer system to perform the steps of:

providing a template dialog of questions including name, medication information, personal information, emergency contacts, insurance information, pharmacy information and medical history;

prompting a user to provide responses to complete the dialog of questions;

storing said responses in said computer system;

map data of said responses to rows of a medication report;

automatically determine an optimal pillbox arrangement of pillbox size and slots based on pre-stored information;

map data of medication information to a placement of pills in said pillbox arrangement so as to create a pillbox map, said pillbox map displaying the shape, color and appearance of pill type medications, dosage instructions and prescribing physician;

generate labels for an actual pillbox;

print out a single report including said rows of said medication report and said pillbox map;

print a set of labels for an actual pillbox.

* * * * *